(12) United States Patent
Ferree

(10) Patent No.: US 9,084,616 B2
(45) Date of Patent: Jul. 21, 2015

(54) METHODS AND APPARATUS FOR TREATING DISC HERNIATION AND PREVENTING THE EXTRUSION OF INTERBODY BONE GRAFT

(75) Inventor: Bret A. Ferree, Cincinnati, OH (US)

(73) Assignee: Anova Corporation, Basking Ridge, NJ (US)

( * ) Notice: Subject to any disclaimer, the term of this patent is extended or adjusted under 35 U.S.C. 154(b) by 947 days.

(21) Appl. No.: 11/546,483

(22) Filed: Oct. 11, 2006

(65) Prior Publication Data

US 2007/0027471 A1   Feb. 1, 2007

Related U.S. Application Data

(63) Continuation of application No. 10/630,445, filed on Jul. 30, 2003, now Pat. No. 7,273,497, which is a continuation of application No. 09/638,241, filed on Aug. 14, 2000, now abandoned, which is a
(Continued)

(51) Int. Cl.
*A61F 2/44* (2006.01)
*A61B 17/16* (2006.01)
(Continued)

(52) U.S. Cl.
CPC .......... *A61B 17/1671* (2013.01); *A61F 2/2846* (2013.01); *A61F 2/30742* (2013.01); *A61F 2/441* (2013.01); *A61F 2/442* (2013.01); *A61F 2/447* (2013.01); *A61F 2/4455* (2013.01); *A61F 2/4611* (2013.01); *A61L 27/3856* (2013.01);
(Continued)

(58) Field of Classification Search
CPC ....... A61F 2/44; A61F 2/4611; A61F 2/4435; A61B 17/70; A61B 17/842; A61B 17/88
USPC .............................. 606/279; 623/17.11–17.16
See application file for complete search history.

(56) References Cited

U.S. PATENT DOCUMENTS

| 3,867,728 A | 2/1975 | Stubstad |
| 3,875,595 A | 4/1975 | Froning |

(Continued)

FOREIGN PATENT DOCUMENTS

| EP | 0700671 | 3/1996 |
| EP | 0277678 | 8/1998 |

(Continued)

OTHER PUBLICATIONS

"Proceedings 14th Annual Meeting" North American Spine Society, Oct. 1999.
(Continued)

*Primary Examiner* — Eduardo C Robert
*Assistant Examiner* — Julianna N Harvey
(74) *Attorney, Agent, or Firm* — Pandiscio & Pandiscio

(57) ABSTRACT

Methods for treating an annulus fibrosis having a defect include inserting a flexible device into the defect. The flexible device is advanced distally beyond an outer layer of the annulus fibrosus. The flexible device is then expanded such that a width of the flexible device is larger than the defect, where the flexible device prevents escape of nucleus pulposus through the defect. The flexible device may have at least two appendages made from a shape-memory metal. Alternatively, the flexible device may have a U-shaped structure that includes a central portion and two legs. The flexible device may also be anchored to the annulus fibrosis and/or the vertebrae.

18 Claims, 13 Drawing Sheets

Related U.S. Application Data continuation-in-part of application No. PCT/US00/14708, filed on May 30, 2000, which is a continuation-in-part of application No. 09/322,516, filed on May 28, 1999, now Pat. No. 6,245,107.

(60) Provisional application No. 60/148,913, filed on Aug. 13, 1999.

(51) Int. Cl.
| | |
|---|---|
| *A61F 2/28* | (2006.01) |
| *A61F 2/30* | (2006.01) |
| *A61L 27/38* | (2006.01) |
| *A61B 17/00* | (2006.01) |
| *A61B 17/02* | (2006.01) |
| *A61F 2/46* | (2006.01) |

(52) U.S. Cl.
CPC ............... *A61B 2017/00261* (2013.01); *A61B 2017/0256* (2013.01); *A61F 2/30744* (2013.01); *A61F 2/30965* (2013.01); *A61F 2/4601* (2013.01); *A61F 2002/2835* (2013.01); *A61F 2002/302* (2013.01); *A61F 2002/3052* (2013.01); *A61F 2002/30093* (2013.01); *A61F 2002/30131* (2013.01); *A61F 2002/30153* (2013.01); *A61F 2002/30224* (2013.01); *A61F 2002/30235* (2013.01); *A61F 2002/30271* (2013.01); *A61F 2002/30283* (2013.01); *A61F 2002/30329* (2013.01); *A61F 2002/30433* (2013.01); *A61F 2002/30441* (2013.01); *A61F 2002/30461* (2013.01); *A61F 2002/30538* (2013.01); *A61F 2002/30556* (2013.01); *A61F 2002/30565* (2013.01); *A61F 2002/30576* (2013.01); *A61F 2002/30579* (2013.01); *A61F 2002/30589* (2013.01); *A61F 2002/30626* (2013.01); *A61F 2002/30677* (2013.01); *A61F 2002/30774* (2013.01); *A61F 2002/30777* (2013.01); *A61F 2002/30784* (2013.01); *A61F 2002/30787* (2013.01); *A61F 2002/30828* (2013.01); *A61F 2002/30909* (2013.01); *A61F 2002/30975* (2013.01); *A61F 2002/444* (2013.01); *A61F 2002/445* (2013.01); *A61F 2002/448* (2013.01); *A61F 2002/4435* (2013.01); *A61F 2002/4445* (2013.01); *A61F 2002/4475* (2013.01); *A61F 2002/4627* (2013.01); *A61F 2002/4628* (2013.01); *A61F 2210/0019* (2013.01); *A61F 2220/0025* (2013.01); *A61F 2220/0041* (2013.01); *A61F 2220/0075* (2013.01); *A61F 2230/0013* (2013.01); *A61F 2230/0019* (2013.01); *A61F 2230/0063* (2013.01); *A61F 2230/0065* (2013.01); *A61F 2230/0069* (2013.01); *A61F 2230/0082* (2013.01); *A61F 2250/0006* (2013.01); *A61F 2250/0009* (2013.01); *A61F 2250/0069* (2013.01); *A61F 2310/00017* (2013.01); *A61F 2310/00023* (2013.01); *A61F 2310/00029* (2013.01); *A61L 2430/38* (2013.01)

(56) References Cited

U.S. PATENT DOCUMENTS

| | | | |
|---|---|---|---|
| 4,349,921 A | 9/1982 | Kuntz | |
| 4,413,359 A | 11/1983 | Akiyama | |
| 4,502,161 A | 3/1985 | Wall | |
| 4,512,338 A | 4/1985 | Balko | |
| 4,532,926 A | 8/1985 | O'Holla | |
| 4,663,358 A | 5/1987 | Hyon | |
| 4,665,906 A | 5/1987 | Jervis | |
| 4,741,330 A | 5/1988 | Hayhurst | |
| 4,743,256 A | 5/1988 | Brantigan | |
| 4,744,364 A | 5/1988 | Kensey | |
| 4,772,287 A | 9/1988 | Ray | |
| 4,781,190 A | 11/1988 | Lee | |
| 4,798,205 A | 1/1989 | Bonomo | |
| 4,801,299 A | 1/1989 | Brendel et al. | |
| 4,834,757 A | 5/1989 | Brantigan | |
| 4,837,285 A | 6/1989 | Berg | |
| 4,852,568 A | 8/1989 | Kensey | |
| 4,863,477 A | 9/1989 | Monson | |
| 4,873,976 A | 10/1989 | Schreiber | |
| 4,890,612 A | 1/1990 | Kensey | |
| 4,904,260 A | 2/1990 | Ray | |
| 4,904,261 A | 2/1990 | Dove et al. | |
| 4,911,718 A | 3/1990 | Lee | |
| 4,917,704 A | 4/1990 | Frey | |
| 4,932,969 A | 6/1990 | Frey | |
| 4,946,378 A | 8/1990 | Hirayama | |
| 4,955,908 A | 9/1990 | Frey | |
| 5,002,576 A | 3/1991 | Fuhrmann | |
| 5,015,255 A | 5/1991 | Kuslich | |
| 5,021,059 A | 6/1991 | Kensey | |
| 5,035,716 A | 7/1991 | Downey | |
| 5,047,055 A | 9/1991 | Bao | |
| 5,053,046 A | 10/1991 | Janese | |
| 5,059,193 A | 10/1991 | Kuslich | |
| 5,059,206 A | 10/1991 | Winters | |
| 5,061,274 A | 10/1991 | Kensey | |
| 5,071,437 A | 12/1991 | Steffee | |
| 5,100,422 A | 3/1992 | Berguer | |
| 5,108,438 A | 4/1992 | Stone | |
| 5,116,357 A | 5/1992 | Eberbach | |
| 5,122,155 A | 6/1992 | Eberbach | |
| 5,123,926 A | 6/1992 | Pisharodi | |
| 5,141,515 A | 8/1992 | Eberbach | |
| 5,147,374 A | 9/1992 | Fernandez | |
| 5,171,259 A | 12/1992 | Inoue | |
| 5,171,278 A | 12/1992 | Pisharodi | |
| 5,171,280 A | 12/1992 | Baumgartner | |
| 5,171,281 A | 12/1992 | Parsons | |
| 5,176,692 A | 1/1993 | Wilk | |
| 5,192,326 A | 3/1993 | Bao | |
| 5,222,974 A | 6/1993 | Kensey | |
| 5,254,133 A | 10/1993 | Seid | |
| 5,258,000 A | 11/1993 | Gianturco | |
| 5,258,043 A | 11/1993 | Stone | |
| 5,263,953 A | 11/1993 | Bagby | |
| 5,269,783 A | 12/1993 | Sander | |
| 5,282,827 A | 2/1994 | Kensey | |
| 5,304,194 A | 4/1994 | Chee | |
| 5,306,311 A | 4/1994 | Stone | |
| 5,312,435 A | 5/1994 | Nash | |
| 5,318,780 A | 6/1994 | Viegas | |
| 5,320,633 A | 6/1994 | Allen | |
| 5,320,644 A | 6/1994 | Baumgartner | |
| 5,342,393 A | 8/1994 | Stack | |
| 5,342,394 A | 8/1994 | Matsuno | |
| 5,356,432 A | 10/1994 | Rutkow | |
| 5,366,460 A | 11/1994 | Eberbach | |
| 5,368,602 A | 11/1994 | de la Torre | |
| 5,370,660 A | 12/1994 | Weinstein | |
| 5,370,697 A | 12/1994 | Baumgartner | |
| 5,376,693 A | 12/1994 | Viegas | |
| 5,383,477 A | 1/1995 | DeMatteis | |
| 5,383,905 A | 1/1995 | Golds | |
| 5,390,683 A | 2/1995 | Pisharodi | |
| 5,397,331 A | 3/1995 | Himpens | |
| 5,397,332 A | 3/1995 | Kammerer | |
| 5,405,360 A | 4/1995 | Tovey | |
| 5,425,772 A | 6/1995 | Brantigan | |
| 5,425,773 A | 6/1995 | Boyd | |
| 5,437,631 A | 8/1995 | Janzen | |
| 5,443,483 A | 8/1995 | Kirsch | |
| 5,456,665 A * | 10/1995 | Postell et al. | 604/103.09 |
| 5,456,720 A | 10/1995 | Schultz | |
| 5,464,407 A | 11/1995 | McGuire | |
| 5,464,439 A | 11/1995 | Gendler | |

(56) References Cited

U.S. PATENT DOCUMENTS

| | | |
|---|---|---|
| 5,496,318 A | 3/1996 | Howland et al. |
| 5,500,000 A | 3/1996 | Feagin |
| 5,507,754 A | 4/1996 | Green |
| 5,514,180 A | 5/1996 | Heggeness |
| 5,520,700 A | 5/1996 | Beyar |
| 5,531,759 A | 7/1996 | Kensey |
| 5,534,028 A | 7/1996 | Bao |
| 5,534,030 A | 7/1996 | Navarro |
| 5,540,715 A | 7/1996 | Katsaros |
| 5,545,178 A | 8/1996 | Kensey |
| 5,545,229 A | 8/1996 | Parsons |
| 5,549,617 A | 8/1996 | Green |
| 5,549,679 A * | 8/1996 | Kuslich .................. 623/17.12 |
| 5,554,191 A | 9/1996 | Lahille et al. |
| 5,556,428 A | 9/1996 | Shah |
| 5,556,429 A | 9/1996 | Felt |
| 5,562,690 A | 10/1996 | Green |
| 5,562,736 A | 10/1996 | Ray |
| 5,562,738 A | 10/1996 | Boyd |
| 5,569,252 A | 10/1996 | Justin |
| 5,571,189 A | 11/1996 | Kuslich |
| 5,582,616 A | 12/1996 | Bolduc |
| 5,587,175 A | 12/1996 | Viegas |
| 5,591,223 A | 1/1997 | Lock |
| 5,613,974 A | 3/1997 | Andreas |
| 5,620,012 A | 4/1997 | Benderev |
| 5,624,463 A | 4/1997 | Stone |
| 5,626,613 A | 5/1997 | Schmieding |
| 5,634,931 A | 6/1997 | Kagel |
| 5,643,329 A | 7/1997 | Solomonow et al. |
| 5,645,084 A | 7/1997 | McKay |
| 5,645,597 A | 7/1997 | Krapiva |
| 5,653,763 A | 8/1997 | Errico et al. |
| 5,658,343 A | 8/1997 | Hauselmann |
| 5,662,683 A | 9/1997 | Kay |
| 5,669,935 A | 9/1997 | Rosenman |
| 5,674,294 A | 10/1997 | Bainville |
| 5,674,296 A | 10/1997 | Bryan |
| 5,676,698 A | 10/1997 | Janzen |
| 5,676,701 A | 10/1997 | Yuan |
| 5,681,310 A | 10/1997 | Yuan |
| 5,681,351 A | 10/1997 | Jamiolkowski |
| 5,683,465 A | 11/1997 | Shinn |
| 5,690,674 A | 11/1997 | Diaz |
| 5,695,525 A | 12/1997 | Mulhauser et al. |
| 5,702,450 A | 12/1997 | Bisserie |
| 5,702,451 A | 12/1997 | Biedermann |
| 5,702,454 A | 12/1997 | Baumgartner |
| 5,702,462 A | 12/1997 | Oberlander |
| 5,709,854 A | 1/1998 | Griffith-Cima |
| 5,716,408 A | 2/1998 | Eldridge |
| 5,716,409 A | 2/1998 | Debbas |
| 5,716,413 A | 2/1998 | Walter |
| 5,716,416 A | 2/1998 | Lin |
| 5,718,862 A | 2/1998 | Thompson |
| 5,725,577 A | 3/1998 | Saxon |
| 5,728,150 A | 3/1998 | McDonald |
| 5,730,744 A | 3/1998 | Justin |
| 5,733,337 A | 3/1998 | Car, Jr. |
| 5,743,917 A | 4/1998 | Saxon |
| 5,746,755 A | 5/1998 | Wood |
| 5,746,765 A | 5/1998 | Rabkin |
| 5,766,246 A | 6/1998 | Mulhauser |
| 5,769,864 A | 6/1998 | Kugel |
| 5,769,893 A | 6/1998 | Shah |
| 5,772,661 A | 6/1998 | Michelson |
| 5,776,183 A | 7/1998 | Kanesaka |
| 5,776,196 A | 7/1998 | Matsuzaki et al. |
| 5,782,844 A | 7/1998 | Yoon |
| 5,782,919 A | 7/1998 | Zdeblick et al. |
| 5,785,705 A | 7/1998 | Baker |
| 5,800,549 A | 9/1998 | Bao |
| 5,800,550 A | 9/1998 | Sertich |
| 5,801,033 A | 9/1998 | Hubbell |
| 5,810,851 A | 9/1998 | Yoon |
| 5,823,994 A | 10/1998 | Sharkey |
| 5,824,008 A | 10/1998 | Bolduc |
| 5,824,082 A | 10/1998 | Brown |
| 5,824,093 A | 10/1998 | Ray et al. |
| 5,824,094 A | 10/1998 | Serhan |
| 5,827,298 A | 10/1998 | Hart |
| 5,827,328 A | 10/1998 | Buttermann |
| 5,836,315 A | 11/1998 | Benderev |
| 5,843,084 A | 12/1998 | Hart |
| 5,846,261 A | 12/1998 | Kotula |
| 5,860,425 A | 1/1999 | Benderev |
| 5,860,977 A | 1/1999 | Zucherman |
| 5,865,845 A | 2/1999 | Thalgott |
| 5,865,846 A | 2/1999 | Bryan |
| 5,865,847 A | 2/1999 | Kohrs et al. |
| 5,865,848 A | 2/1999 | Baker |
| 5,879,366 A | 3/1999 | Shaw |
| 5,885,287 A | 3/1999 | Bagby |
| 5,888,220 A | 3/1999 | Felt |
| 5,888,226 A | 3/1999 | Rogozinski |
| 5,888,227 A | 3/1999 | Cottle |
| 5,893,889 A | 4/1999 | Harrington |
| 5,893,890 A | 4/1999 | Pisharodi |
| 5,895,427 A | 4/1999 | Kuslich et al. |
| 5,897,593 A | 4/1999 | Kohrs et al. |
| 5,906,616 A | 5/1999 | Pavlov et al. |
| 5,916,225 A | 6/1999 | Kugel |
| 5,919,235 A | 7/1999 | Husson |
| 5,922,026 A | 7/1999 | Chin |
| 5,928,284 A | 7/1999 | Mehdizadeh |
| 5,935,147 A | 8/1999 | Kensey |
| 5,954,716 A | 9/1999 | Sharkey |
| 5,954,767 A | 9/1999 | Pajotin |
| 5,957,939 A | 9/1999 | Heaven |
| 5,972,000 A | 10/1999 | Beyar |
| 5,972,007 A | 10/1999 | Sheffield |
| 5,972,022 A | 10/1999 | Huxel |
| 5,976,174 A | 11/1999 | Ruiz |
| 5,976,186 A | 11/1999 | Bao |
| 5,980,504 A | 11/1999 | Sharkey |
| 5,989,291 A | 11/1999 | Ralph et al. |
| 6,001,130 A | 12/1999 | Bryan |
| 6,007,570 A | 12/1999 | Sharkey |
| 6,007,575 A | 12/1999 | Samuels |
| 6,019,793 A | 2/2000 | Perren |
| 6,024,754 A | 2/2000 | Engelson |
| 6,027,527 A | 2/2000 | Asano |
| 6,060,053 A | 5/2000 | Atala |
| 6,066,325 A | 5/2000 | Wallace et al. |
| 6,077,987 A | 6/2000 | Breitbart et al. |
| 6,093,205 A | 7/2000 | McLeod et al. |
| 6,102,950 A | 8/2000 | Vaccaro |
| 6,117,174 A | 9/2000 | Nolan |
| 6,126,682 A | 10/2000 | Sharkey |
| 6,140,452 A | 10/2000 | Felt |
| 6,143,032 A | 11/2000 | Schafer et al. |
| 6,146,380 A | 11/2000 | Racz |
| 6,179,875 B1 | 1/2001 | Von Strempel |
| 6,180,848 B1 | 1/2001 | Flament |
| 6,183,518 B1 | 2/2001 | Ross |
| 6,187,048 B1 | 2/2001 | Milner et al. |
| 6,190,414 B1 | 2/2001 | Young et al. |
| 6,193,757 B1 | 2/2001 | Foley et al. |
| 6,197,586 B1 | 3/2001 | Bhatnagar et al. |
| 6,206,921 B1 | 3/2001 | Guagliano |
| 6,206,922 B1 | 3/2001 | Zdeblick et al. |
| 6,221,109 B1 | 4/2001 | Geistlich et al. |
| 6,224,630 B1 | 5/2001 | Bao |
| 6,231,615 B1 | 5/2001 | Preissman |
| 6,245,107 B1 | 6/2001 | Ferree |
| 6,245,108 B1 | 6/2001 | Biscup |
| 6,261,289 B1 * | 7/2001 | Levy .................. 606/63 |
| 6,264,695 B1 | 7/2001 | Stoy |
| 6,340,369 B1 | 1/2002 | Ferree |
| 6,352,557 B1 | 3/2002 | Ferree |
| 6,371,990 B1 | 4/2002 | Ferree |
| 6,402,750 B1 | 6/2002 | Atkinson |
| 6,419,702 B1 | 7/2002 | Ferree |
| 6,419,704 B1 | 7/2002 | Ferree |

(56) References Cited

U.S. PATENT DOCUMENTS

| | | |
|---|---|---|
| 6,425,919 B1 * | 7/2002 | Lambrecht ................ 623/17.16 |
| 6,428,576 B1 | 8/2002 | Haldimann |
| 6,436,143 B1 | 8/2002 | Ross |
| 6,482,235 B1 | 11/2002 | Lambrecht |
| 6,488,710 B2 | 12/2002 | Besselink |
| 6,491,724 B1 | 12/2002 | Ferree |
| 6,508,839 B1 | 1/2003 | Lambrecht et al. |
| 6,969,404 B2 | 11/2005 | Ferree |
| 2002/0077701 A1 | 6/2002 | Kuslich |
| 2002/0147497 A1 | 10/2002 | Belef et al. |
| 2002/0198599 A1 | 12/2002 | Haldimann |
| 2003/0074075 A1 | 4/2003 | Thomas et al. |

FOREIGN PATENT DOCUMENTS

| | | |
|---|---|---|
| EP | 0722700 | 12/1998 |
| EP | 1180978 | 5/2005 |
| FR | 2639823 | 6/1990 |
| JP | 5508795 | 12/1993 |
| JP | 7000430 | 1/1995 |
| JP | 8098851 | 4/1996 |
| JP | 10507386 | 7/1998 |
| WO | WO 92/10982 | 7/1992 |
| WO | WO-95/31946 | 11/1995 |
| WO | WO-95/34331 | 12/1995 |
| WO | WO 96/11642 | 4/1996 |
| WO | WO 97/26847 | 7/1997 |
| WO | WO 97/27893 | 8/1997 |
| WO | WO-97/30638 | 8/1997 |
| WO | WO-98/17190 | 4/1998 |
| WO | WO 98/20939 | 5/1998 |
| WO | WO-98/34552 | 8/1998 |
| WO | WO-99/00074 | 1/1999 |
| WO | WO-99/02108 | 1/1999 |
| WO | WO-99/02214 | 1/1999 |
| WO | WO-99/03422 | 1/1999 |
| WO | WO 99/05992 | 2/1999 |
| WO | WO-99/30651 | 6/1999 |
| WO | WO-99/47058 | 9/1999 |
| WO | WO-99/61084 | 12/1999 |
| WO | WO-99/61840 | 12/1999 |
| WO | WO-99/62439 | 12/1999 |
| WO | WO-00/42953 | 7/2000 |
| WO | WO-00/62832 | 10/2000 |
| WO | WO-01/10316 | 2/2001 |
| WO | WO-01/10318 | 2/2001 |
| WO | WO-01/21246 | 3/2001 |
| WO | WO-01/28464 | 4/2001 |
| WO | WO-01/45577 | 6/2001 |

OTHER PUBLICATIONS

"Proceedings 13th Annual Meeting" North American Spine Society, Oct. 1998.

Goel, V.K., et al., "Mechanical Properties of Lumbar Spinal Motion Segments as Affected by Partial Disc Removal," Spine, 11(10):1008-1012 (1986).

Ahlgren, B.D., et al, "Anular Incision Technique on the Strength and Multidirectional Flexibility of the Healing Intervertebral Disc," Spine, 19(8): 948-954 (1994).

Barr, J.S., "Ruptured Intervertebral Disc and Sciatic Pain," J. of Bone and Joint Surgery, 29, (2): 429-437 (1947).

Postacchini, F., "Spine Update Results of Surgery Compared With Conservative Management of Lumbar Disc Herniations," Spine, 21 (11): 1383-1387 (1996).

Rogers, L.A., "Experience With Limited versus Extensive Disc Removal in Patients Undergoing Microsurgical Operations for Ruptured Lumbar Discs," Neurosurgery, 22(1):82-85 (1988).

Brinckmann, P., et al., "Change of Disc Height, Radial Disc Bulge, and Intradiscal Pressure from Discectomy An in Vitro Investigation on Human Lumbar Discs," Spine, 16(6):641-646 (1991).

Balderston, R.A., et al., "The Treatment of Lumbar Disc Herniation: Simple Fragment Excision Versus Disc Space Curettage," J. of Spinal Disorders, 4(1):22-25 (1991).

Hanley, E.N., Jr. et al., "The Development of Low-Back Pain after Excision of a Lumbar Disc," J. of Bone and Joint Surgery, 71A(5):719-721 (1989).

Heggeness, M.H., et al., "Discography of Lumbar Discs After Surgical Treatment for Disc Herniation," Spine, 22(14):1606-1609 (1997).

Kayama, S., et al., "Incision of the Anulus Fibrosus Induces Nerve Root Morphologic Vascular, and Functional changes," Spine, 21(22):2539-2543 (1996).

Tibrewal, S.B., et al., "Lumbar Intervertebral Disc Heights in Normal Subjects and Patients with Disc Herniation," Spine, 10(5):452-454 (1985).

Cathen, Joseph, C., M.D., "Microsurgical Annular Reconstruction (Annuloplasty) Following Lumbar Microdiscectomy: Preliminary Report of a New Technique," Abstract for Poster Presentation, AANS/CNS Section on Disorders of the Spine and Peripheral Nerves Annual Meeting, 1999.

Nucléoplastie Inter-Somatique Par Voie Postérieure Per-Dissectomie: Concept et Étude Éxpérimentale. J.L. Husson et al., Restabilisation Inter-Somatique Du Rachis Lombaire, Sauramps Medical, 1996 pp. 311-320 [and English translation].

Yasargil, M.G., "Microsurgical Operation of Herniated Lumbar Disc," p. 81 1977.

Kayama, S. et al., "Inciscion of the Annulus Fibrosus Induces Nerve Root Morphologic, Vascular, and Functional Changes: An Experimental Study," Spine, 21 (22): 2539-2543, (1996).

Steven L, Prick et al., Lumbar Intervertebral Disc Transfer: A Canine Study, Spine, 1994, pp. 1826-1835, vol. 19, No. 16.

Tulberg, T. et al., "Radiographic Changes After Lumbar Discectomy: Sequential Enhanced Computed Tomography in Relation to Clinical Observation," Spine, 18 (7): 843-850, (1993).

* cited by examiner

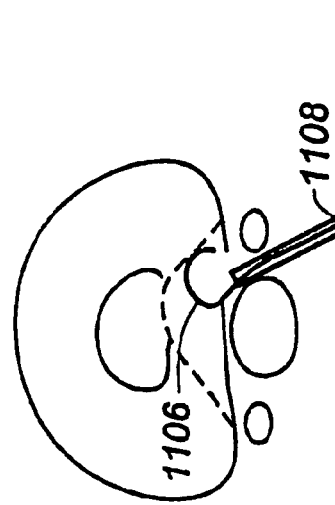
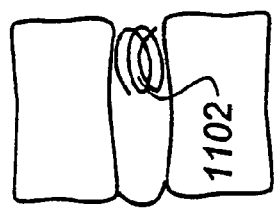
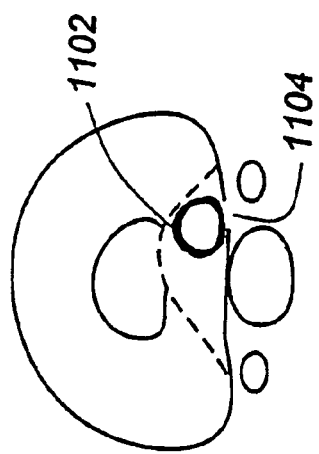
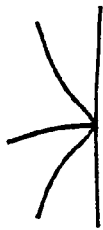
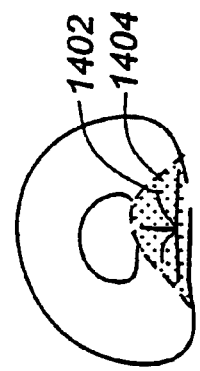
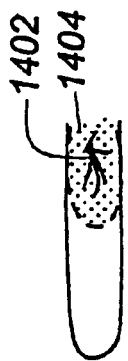
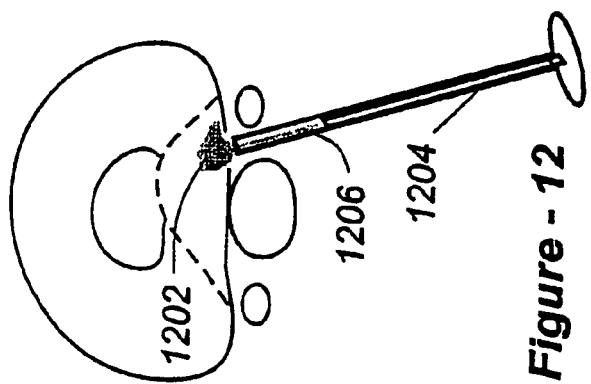

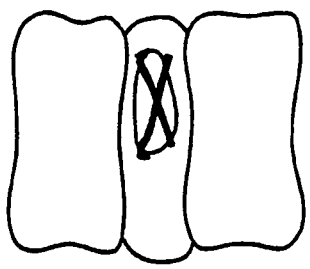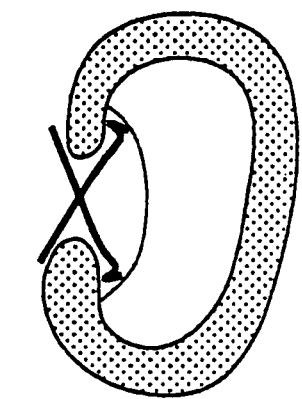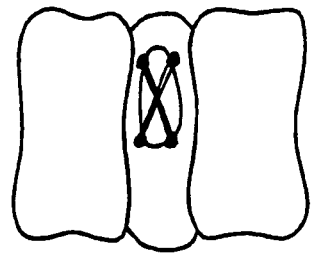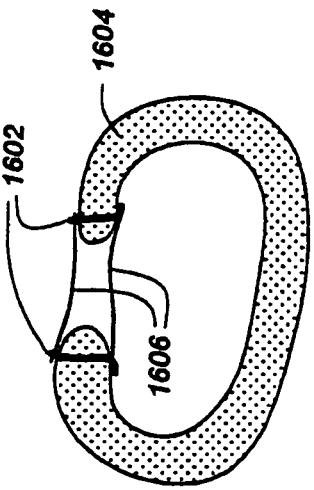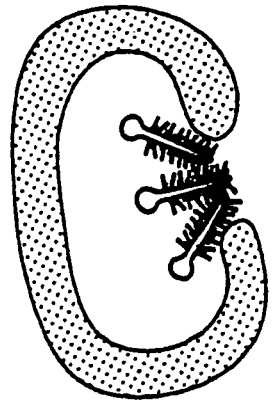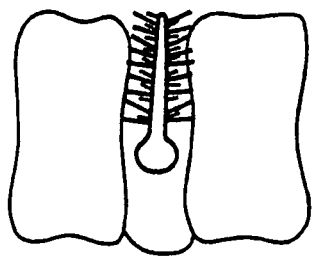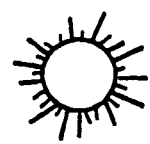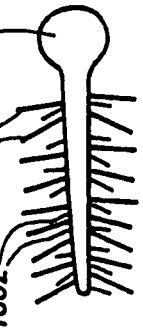

(DISTRACTION)

(DISTRACTION)

METHODS AND APPARATUS FOR TREATING DISC HERNIATION AND PREVENTING THE EXTRUSION OF INTERBODY BONE GRAFT

REFERENCE TO RELATED APPLICATIONS

This is a continuation of U.S. patent application Ser. No. 10/630,445, filed Jul. 30, 2003, which is a continuation of U.S. patent application Ser. No. 09/638,241, filed Aug. 14, 2000, which is a continuation-in-part of International Patent Application No. PCT/US00/14708, filed May 30, 2000, which is a continuation-in-part of and claims the benefit under 35 USC §119 of U.S. patent application Ser. No. 09/322,516, filed May 28, 1999, now U.S. Pat. No. 6,245,107. The '241 application also claims priority from U.S. Provisional Patent Application Ser. No. 60/148,913, filed Aug. 13, 1999. The entire content of each application and patent is hereby expressly incorporated by reference in its entirety.

FIELD OF THE INVENTION

This invention relates generally to the prosthetic appliances and, in particular, to devices for occluding intervertebral disc defects and instrumentation associated with introducing such devices.

BACKGROUND OF THE INVENTION

Several hundred thousand patients undergo disc operations each year. Approximately five percent of these patients will suffer recurrent disc herniation, which results from a void or defect which remains in the outer layer (annulus fibrosis) of the disc after surgery involving partial discectomy.

Reference is made to FIG. 1A, which illustrates a normal disc as viewed from the feet of a patient up toward the head. The nucleus pulposus 102 is entirely surrounded by the annulus fibrosis 104 in the case of healthy anatomy. Also shown in this cross section is the relative location of the nerves 106. FIG. 1B illustrates the case of the herniated disc, wherein a portion of the nucleus pulposus has ruptured through a defect in the annulus fibrosis, resulting in a pinched nerve 110. This results in pain and further complications, in many cases.

FIG. 1C illustrates the post-operative anatomy following partial discectomy, wherein a space 120 remains adjacent a hole or defect in the annulus fibrosis following removal of the disc material. The hole 122 acts as a pathway for additional material to protrude into the nerve, resulting in the recurrence of the herniation. Since thousands of patients each year require surgery to treat this condition, with substantial implications in terms of the cost of medical treatment and human suffering, any solution to this problem would welcomed by the medical community.

SUMMARY OF THE INVENTION

The subject invention resides in methods and apparatus for treating disc herniation, which may be defined as the escape of nucleus pulposus through a void or defect in the annulus fibrosis of a spinal disc situated between upper and lower vertebra. In addition to preventing the release of natural disc materials, the invention may also be used to retain bone graft for fusion, therapeutic and artificial disc replacement materials. The invention is particularly well suited to the minimization and prevention of recurrent disc herniation, in which case the defect is a hole or void which remains in the annulus fibrosis following disc operations involving partial discectomy.

In broad, general terms, to correct defects of this type, the invention provides a conformable device which assumes a first shape associated with insertion and a second shape or expanded shape to occlude the defect. The device may take different forms according to the invention, including solidifying gels or other liquids or semi-liquids, patches sized to cover the defect, or plugs adapted to fill the defect.

The device is preferably collapsible into some form for the purposes of insertion, thereby minimizing the size of the requisite incision while avoiding delicate surrounding nerves. Such a configuration also permits the use of instrumentation to install the device, including, for example, a hollow tube and a push rod to expel the device or liquefied material out of the sheath for use in occluding the disc defect.

A device according to the invention may further include one or more anchors to assist in permanently affixing the device with respect to the defect. For example, in the embodiment of a mesh screen, the anchors may assume the form of peripheral hooks configured to engage with the vertebra on either side of the disc. The invention further contemplates a distracting tool used to force the anchors into the vertebra. Such a tool would preferably feature a distal head portion conformal to the expanded shape of the device, enabling the surgeon to exert force on the overall structure, thereby setting the anchors.

BRIEF DESCRIPTION OF THE DRAWINGS

FIG. 11A illustrates an alternative embodiment of the invention wherein a coiled wire is used to occlude a disc defect;

FIG. 11B is a side-view representation of the coiled wire of FIG. 11A;

FIG. 11C illustrates how a wire with a coiled memory shape may be straightened and introduced using a plunger-type instrument;

FIG. 12 illustrates yet a different alternative embodiment of the invention wherein a material in liquid or gel form may be introduced into a defect, after which it hardens or solidifies to prevent further rupturing;

FIG. 13A illustrates yet a further alternative embodiment of the invention, in the form of a stent having a plurality of leaves;

FIG. 13B illustrates the alternative of FIG. 13A, wherein the leaves assume a second shape associated with defect occlusion, preferably through memory affect;

FIG. 14A illustrates an aspect of the invention wherein a conformable device is suspended within a gel or other resilient material for defect occlusion;

FIG. 14B is a side-view drawing of the embodiment of FIG. 14A;

FIG. 16A is a top-view, cross-sectional drawing of a version of the invention utilizing posts or darts and sutures;

FIG. 16B is a side-view drawing of the embodiment of FIG. 16A;

FIG. 17A shows how posts or darts may be criss-crossed to form a barrier;

FIG. 17B is a side-view drawing of the configuration of FIG. 17A;

FIG. 18A is a side-view drawing of a barbed post that may be used for occlusion according to the invention;

FIG. 18B is an on-access view of the barbed post;

FIG. 18C illustrates how a single larger barbed post may be used for defect occlusion;

FIG. 18D illustrates how the barbed post of FIGS. 18A and 18B may be used in plural fashion to occlude a defect;

DETAILED DESCRIPTION OF THE INVENTION

Figure 1A:
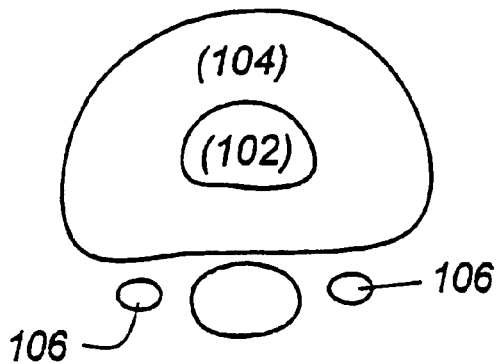
FIG. 1A is a cross section of a human disc exhibiting normal anatomy.
Figure 1B:
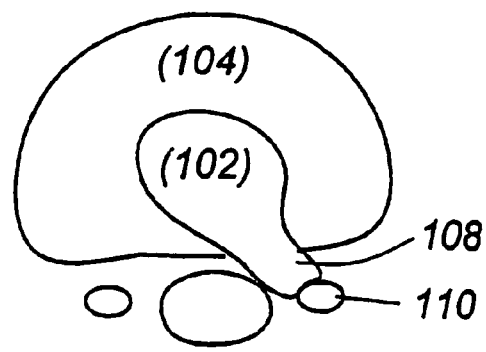
FIG. 1B is a cross section used to illustrate a disc herniation.
Figure 1C:
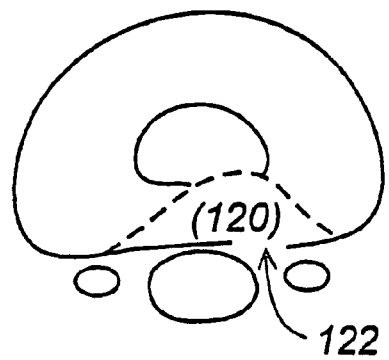
FIG. 1C is a drawing of a disc following a partial discectomy, showing how a space or void remains in the annulus fibrosis.
Figure 2:
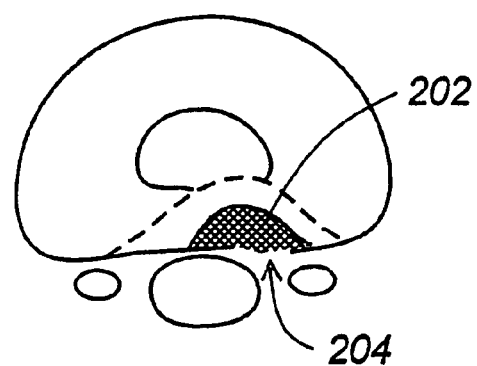
FIG. 2 is a drawing which illustrates a preferred embodiment of the invention in the form of a flexible stent used to occlude a defect in the annulus fibrosis to minimize recurrent disc herniation.

Having discussed the problems associated with post-operative partial discectomy with respect to FIGS. 1A-1C, reference will now be made to FIG. 2, which illustrates a preferred embodiment of the invention, wherein a device in the form of a stent 202 is used to occlude a defect 204 in a human disc, as shown. In this preferred embodiment, the device is composed of a flexible material, which may be cloth, polymeric or metallic. For reasons discussed below, a titanium mesh screen is preferred with respect to this embodiment of the invention.

A flexible device is also preferred because the surgeon is presented with a very small working area. The incision through the skin is typically on the order of 1 to 1.5 inches in length, and the space at the disc level is approximately 1 centimeter on the side. As a consequence, the inventive device and the tools associated with insertion and fixation described below must be sufficiently narrow to fit within these confines.

Figure 3A:
FIG. 3A is a drawing of an applicator used to insert the flexible mesh stent embodiment of FIG. 2.
Figure 3B:
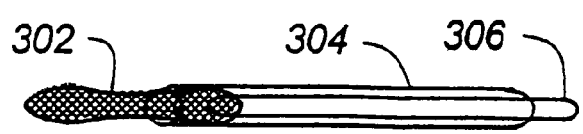
FIG. 3B shows the applicator of FIG. 3A with the stent partially expelled.
Figure 3C:
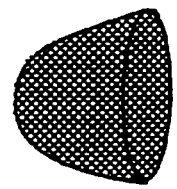
FIG. 3C illustrates a fully expanded shape assumed by the device of FIG. 2 following removal of the insertion tool.

As shown in FIGS. 3A-3C, a flexible screen enables the device to be collapsed into an elongated form 302, which, in turn, facilitates introduction into a sheath 304 associated with insertion. A push rod 306 may then be introduced into the other end of the sheath 304, and either the sheath pulled backwardly or the push rod pushed forwardly, or both, resulting in the shape shown in FIG. 3C, now suitable for implantation.

Figure 4A:
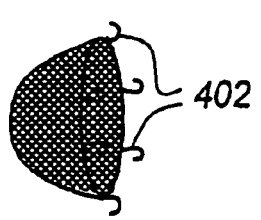
FIG. 4A illustrates the addition of optional peripheral anchors around the stent in the FIG. 4 to assist in fixation.
Figure 4B:
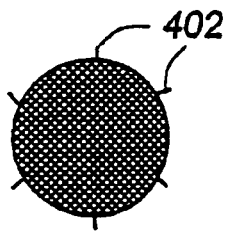
FIG. 4B is an end view of the device of FIG. 4A including the peripheral anchors.
Figure 5:
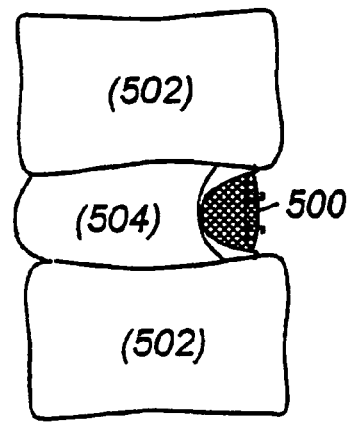
FIG. 5 is a side-view drawing of the device of FIGS. 4A and 4B anchored into upper and lower vertebra bounding the herniated disc.

To further assist in fixation with respect to the surrounding physiology, anchors 402 may be provided around a peripheral edge of the device, as shown in FIG. 4A. FIG. 4B shows an end view of the device of FIG. 4A, and FIG. 5 illustrates the device with anchors generally at 500, being fixed relative to a defective disc 504 bounded by upper and lower vertebrae at 502. It will be apparent to those of skill that each of the devices disclosed herein may be made in different sizes, having varying peripheral dimensions, for example, to match differently sized defects.

Figure 6A:
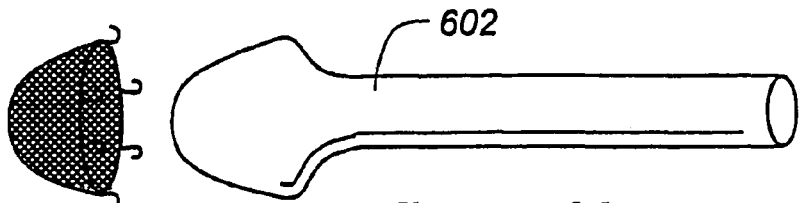
FIG. 6A illustrates an optional distraction tool used to set the anchors of the device of FIGS. 4 and 5 into the vertebra.
Figure 6B:
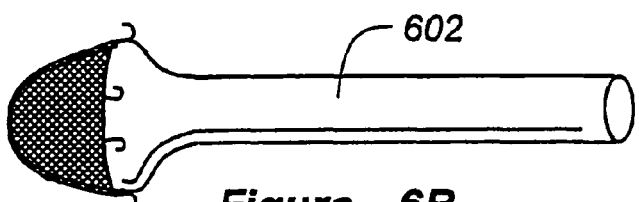
FIG. 6B shows how the distracting tool would be inserted into the device to effectuate distraction.

FIGS. 6A and 6B illustrate how a distracting tool 602 may be used to force the anchors into the vertebrae. That is, having introduced the device into the approximate area, the tool 602, having a forward shape corresponding to that of the expanded mesh shape, may be; introduced therein, as shown in FIG. 6B. With force being applied to the tool 602, the anchors may be permanently set into the surrounding bone/tissue.

Figure 7A:
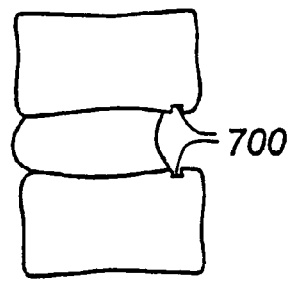
FIG. 7A is a side-view drawing in partial cross-section illustrating the way in which notches may be made to adjoining vertebra to receive a device according to the invention.
Figure 7B:
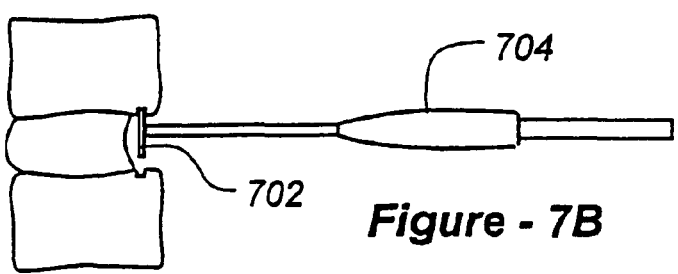
FIG. 7B is a drawing of a tool which may be used to form the notches depicted in FIG. 7A.
Figure 7C:
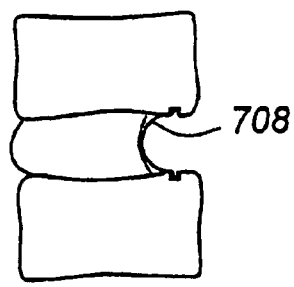
FIG. 7C illustrates the way in which a flexible body may be retained by the notches described with respect to FIGS. 7A and 7B.
Figure 8:
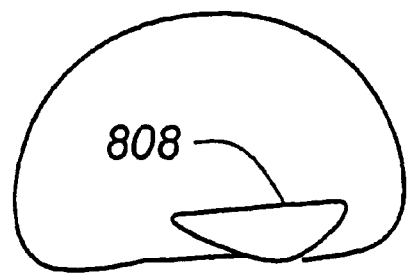
FIG. 8 illustrates an alternative orientation of a flexible body having a convex surface facing outwardly with respect to the wall of the disc being repaired.

FIG. 7A illustrates an alternative approach to fixation, wherein one or more notches 700 may be made into the upper and lower vertebra, preferably through the use of an air-operated drill 704 shown in FIG. 7B, having a cutting wheel 702 adapted for such a purpose. FIG. 7C illustrates the way in which a flexible body 708 may be retained by the notches 700 described with respect to FIGS. 7A and 7B. FIG. 8 illustrates an alternative orientation of a flexible body having a convex surface facing outwardly with respect to the wall of the disc being repaired.

Figure 9A:
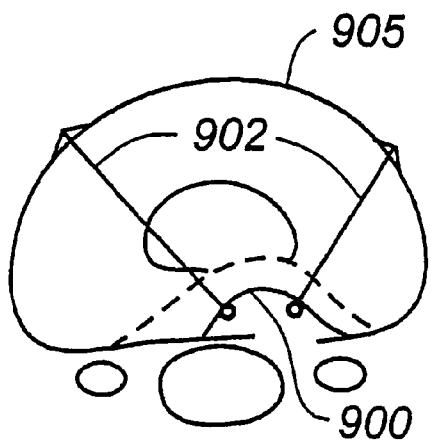
FIG. 9A illustrates how the device according to the invention may be fixed with anchors that penetrate through the disc to be captured at the outer wall thereof.
Figure 9B:
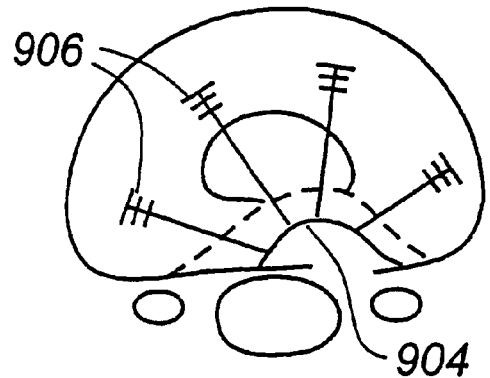
FIG. 9B illustrates an alternative use of anchors which remain within the body of the disc material and do not penetrate its outer wall.

FIG. 9A illustrates a further alternative associated with fixation wherein anchors 902 which penetrate the outer wall of the disc 905 are used to hold a flexible repair device 900 in place as shown. FIG. 9B shows yet a further alternative fixation modality, wherein disc anchors 906, which do not penetrate the outer wall of the disc, but, rather remain there within, are used to hold the device 904 in place.

Figure 9C:
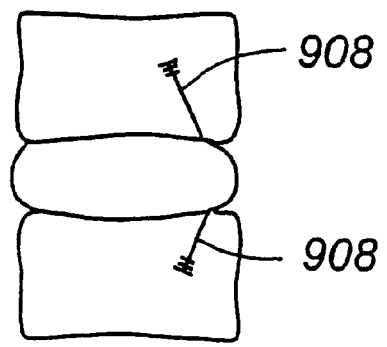
FIG. 9C illustrates an alternative method of fixation, wherein bone anchors are introduced into the vertebrae on either side of the disc in need of repair, as opposed to anchors deployed within or through the disc itself.

FIG. 9C illustrates yet a further alternative mode of fixation, wherein anchors 908 are used to hold the device to upper and lower vertebra, as opposed to the anchors of FIGS. 9A and 9B, which are used with respect to the disc. Regardless of whether fixation takes place within the vertebra or within the disc, it will be noted that according to the preferred embodiment of the invention, both the device used to occlude the defect and the fixation means are sufficiently flexible that the defect remains occluded with movement of the spine, that is, with the patient leaning forwardly and backwardly which will tend to change the spacing between the upper and lower vertebra.

Figure 10:
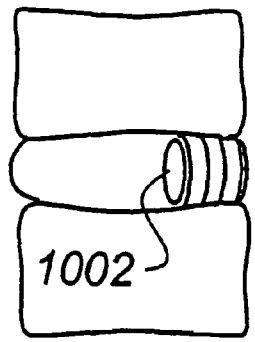
FIG. 10 illustrates an alternative device according to the invention in the form of a resilient plug.

FIG. 10 illustrates yet a different embodiment of the invention wherein, as opposed to a piece of flexible material or mesh, a resilient plug 1002 is instead utilized to occlude the disc defect. As in the case of the flexible sheath-like embodiments described above, such plugs are preferably offered in different sizes to correlate with differently sized defects.

In terms of a preferred material, a device according to the invention will therefore remain sufficiently flexible during movement while being capable of exerting continuous outward forces and withstanding repetitive compression and distraction of millions of cycles. The device would, therefore, preferably be made of a material that has these characteristics, while, additionally being radio-opaque for X-ray imaging, without producing too many unwanted artifacts in magnetic resonance imaging. A wire mesh of titanium is therefore preferable, since this has the proper X-ray/MRI characteristics while exhibiting the requisite flexibility for the cyclic flexion and extension. With respect to the embodiment of FIG. 10, a resilient, rubber-like material may be used to occlude the defect as shown in the drawing from a side-view perspective.

The invention is not limited in the sense that any conformable device may be used with a first shape permitting the device to be introduced into the defective area and a second shape wherein the device includes a defect. As shown in FIGS. 11A-11C, for example, a wire 1102 having a "memory effect" may be used, preferably having a final diameter which is larger than void 104. FIG. 11B shows the coil 102 in cross-section between upper and lower vertebra. Preferably, this embodiment would use a metal wire that may be straightened, but retain the memory of its coiled shape. As such, the apparatus of FIG. 11C may be used to introduce the wire in straightened form 1108 with a plunger 1110, such that as the wire exits at 1106, it returns to its memorized state of a coil (or alternative second shape operative to include the defect).

As yet a different alternative mode of introduction, a material may be injected into the disc in liquid form, then allowed to hardened into a size sufficient to occlude the annular hole. As shown in FIG. 12, material 1202 may be injected into the void of the disc space using a plunger 1204 inserted into a tube 1206. Upon introduction in this manner, the liquid would then solidify, forming a resilient plug.

Various materials may be utilized for this purpose, including various polymers which are caused to solidify by various means, including thermal or optical activation, or chemical reaction as part of multi-part compounds. A preferred material with respect to this embodiment would be a hydrogel. Hydrogels may be placed into the disc in a dehydrated state, and, once inside the disc, they imbibe water. After hydration, hydrogels have the same biomechanical properties as a natural nucleus and, in addition, as the hydrogels swell, they become too large to extrude back through the annular window. U.S. Pat. Nos. 5,047,055 and 5,192,326 provide a listing of hydrogels, certain of which are applicable to this invention.

An elastomer may be used as an alternative to a hydrogel or other material. A number of elastomers may be suited to the invention, including a silicon elastomer, which comprises a cured dimethylsiloxane polymer and Hexsyn, having a composition of one-hexane with three to five percent methylhexaiene. A preformed elastomer may be inserted into the inclusion upon curing or, alternatively, as discussed with reference to FIG. 12, may be injected into the disc space and liquid form. Chemicals may be added to accelerate curing, as discussed above, or, a hot or cold probe, or UV light may be introduced to facilitate or accelerate the curing process. Preferably, such materials would include a radio-opaque additive which would enable the physician to verify the position of the implant with an X-ray. Ideally, the radio-opaque additive would not change the mechanical properties of the gel or elastomer, and would ideally incorporate contrast throughout to enhance detail.

Now making to FIGS. 13 and 14, FIGS. 13A and 13B illustrate an alternative type of stent having leaves or other appendages that may be folded into a compact state for insertion, FIG. 13A, and which expand, through memory affect, for example, to a state such as that shown in FIG. 13B. A stent such as this, as well as other devices disclosed herein such as the coil form of FIG. 11, may be used in conjunction with a gel or other void-filling material as described above. As shown in FIG. 14A, a stent 1402 of the type shown with respect to FIG. 13B, may be introduced into the void, after which the remaining volume of the void may be filled with a material 1404 which solidifies into a resilient material. FIG. 14B is a side-view drawing of the embodiment of FIG. 14A. An expandable stent of this kind may be incorporated into the elastomer or other resilient material to help prevent migration of the prosthesis through the annular hole. In contrast to embodiments of the invention wherein a stent is used independently, in this particular embodiment, the stent would preferably not touch vertebra, since it would be surrounded entirely by the elastomer or other gel material.

Figure 15B:
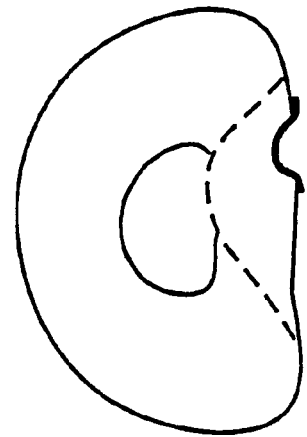
FIGS. 15A-15E are drawings which show various different alternative embodiments according to the invention wherein a patch is used inside and/or outside of a void in need of occlusion.
Figure 15E:
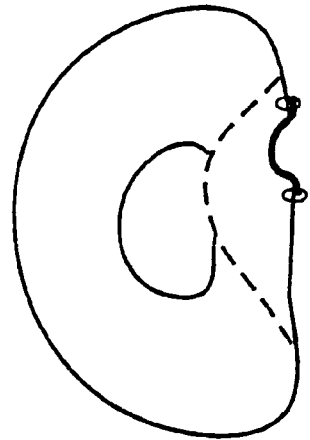
Figure 15D:
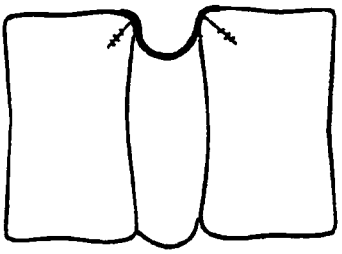
Figure 15A:
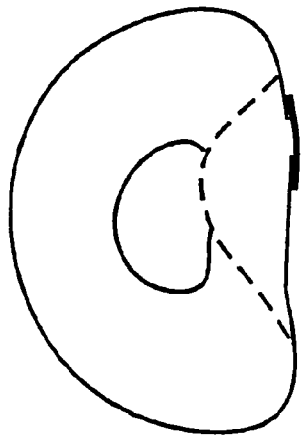
Figure 15C:
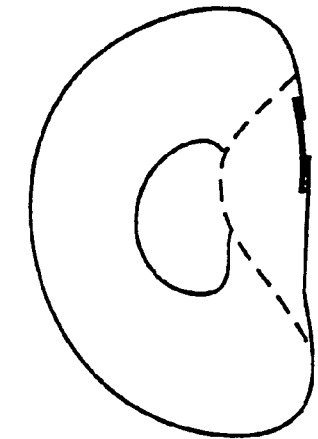

FIGS. 15A-15E illustrate various alternative embodiments according to the invention wherein a patch material is used inside, outside, or partially inside and outside of a defect to be blocked. FIG. 15A illustrates a flat patch attached onto the outside of the disc. FIG. 15B illustrates a patch attached on the outside but wherein a central portion extends inwardly into the void. FIG. 15C illustrates a patch disposed within the disc to block the defect. FIG. 15D illustrates how a patch may be anchored to the bone above and below the disc, and FIG. 15E illustrates how the patch may be anchored to the disc itself. The patch material be a fiber, including natural materials, whether human, non-human or synthetic; an elastomer; plastic; or metal. If a fiber material is used, it may be selected so as to promote tissue in-growth. Growth of a patient's tissue into the material would assure a more permanent closure of the annular window. The patch may be attached within appropriate means, including stitches, staples, glue, screws or other special anchors.

In addition to the use of patches attached with sutures, staples or other materials, the annular defect may be closed with staples or other devices which attach to the annulus without the need for patch material. For example, as shown in FIG. 16A, darts 1602 may be inserted through the wall of the annulus 1604, then linked with sutures 1606, preferably in woven or criss-crossed fashion, as shown in FIG. 16B. As an alternative, appropriately shaped darts 1702 may be criss-crossed or otherwise interlocked to the close the annular hole, as shown in the top-view cross-section drawing of FIG. 17A or a side-view of FIG. 17B.

The use of flexible stents as described elsewhere herein may take on other forms, as shown in FIGS. 18A-18D. The device of FIG. 18A, for example, preferably includes a body 1802, preferably including a blunt anterior end to prevent penetration of the anterior annulus, and outer spikes 1806, preferably having different lengths, as best seen in the on-axis view of FIG. 18B. Such a stent configuration may provide more areas of contact with the vertebral end plates, thereby decreasing the chances of stent extrusion. As shown in FIG. 18C, the longer spikes 1806 are configured to bend during insertion, thereby preventing posterior extrusion. The shorter spikes, 1806', are sized so as not to engage the vertebrae, and therefore may be made thicker to prevent deflection by disc material. As an option, the shorter spikes 1806' may also be angled in the opposite direction as compared to the longer spikes 1806 to resist migration of the disc material. As yet a further option, the longer spikes may vary in length on the same stent so as to be conformal to the vertebral end plate concavity. As shown in FIG. 18D, multiple spike stents of this kind may be inserted so as to interlock with one another, thereby preventing migration of the group.

Figure 19A:
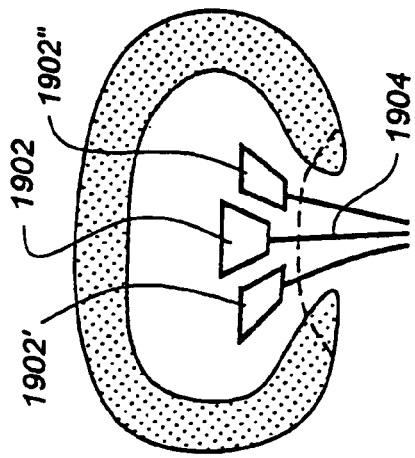
FIG. 19A is a drawing which shows how shaped pieces may be inserted to close off an opening.
Figure 19B:
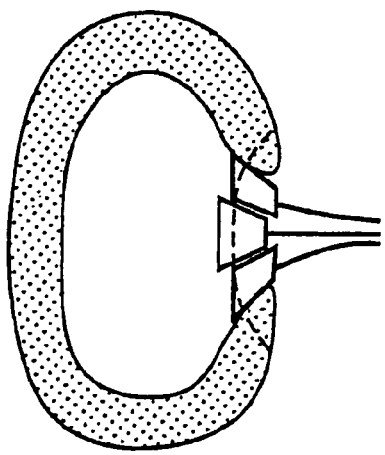
FIG. 19B continues the progression of FIG. 19A, with the pieces being pulled together.
Figure 19C:
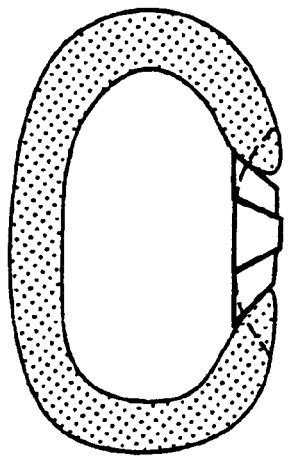
FIG. 19C illustrates the pieces of FIGS. 19A and 19B in a snapped-together configuration.
Figure 20C:
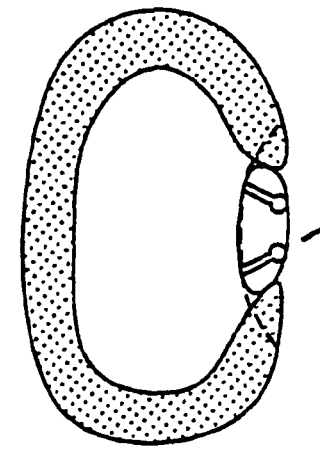
FIGS. 20A-20E are a progression of drawings which show how a shaped body may be held into place with one or more wires to block off a defect.
Figure 20B:
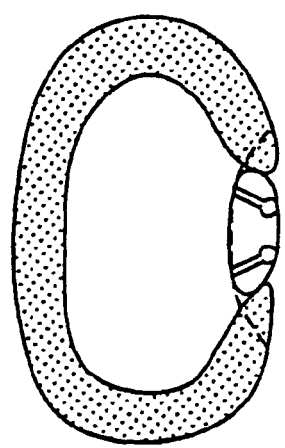
Figure 20E:
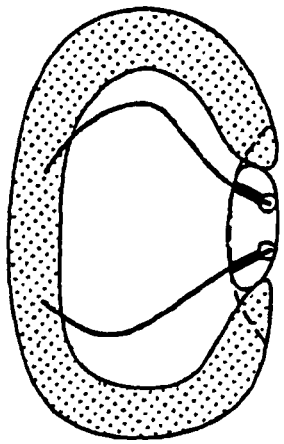
Figure 20D:
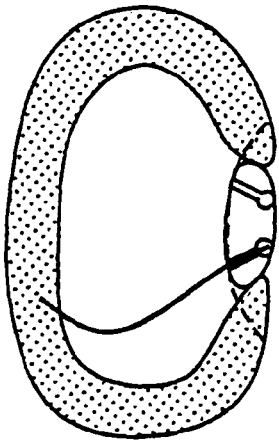
Figure 20A:
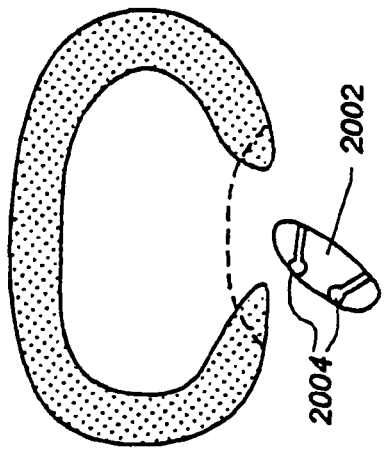

As shown in FIGS. 19A-19C, shapes other than spiked stents may be used in interlocking fashion. In FIG. 19A, a first piece 1902 is inserted having a removable handle 1904, after which pieces 1902' and 1902" are inserted, each having their own removable handles, as shown. In FIG. 19B, the handles are pulled, so as to bring the pieces together, and in FIG. 19C, the handles are removed, and the pieces are either snapped together or, through the use of suitable material, sutured into place. FIGS. 20A-20E illustrate a different configuration of this kind, wherein a body 2002 having anchor or wire-receiving apertures 2004 is inserted into the annular hole, as shown in FIG. 20B, at which time a wire 2006 is inserted through the body 2002 as shown in FIG. 20C. As shown in FIG. 20D, the wire is installed sufficient to lock one portion of the body into place, and this is followed with a wire on the opposite side, thereby holding the body 2002 in a stabilized manner. It will be appreciated that although multiple wires or anchors are used in this configuration, bodies configured to receive more or fewer wires or anchors are also anticipated by this basic idea.

Figure 21A:
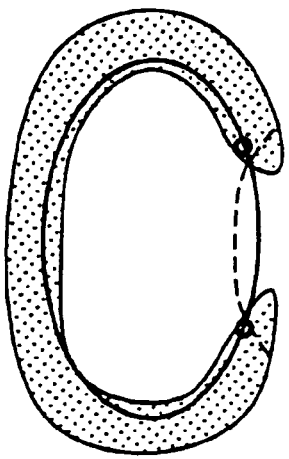
FIGS. 21A-21C illustrate how wires may be used in conjunction with snap-on beads to occlude a defect.
Figure 21B:
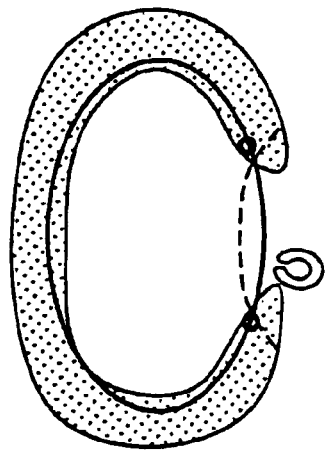
Figure 21C:
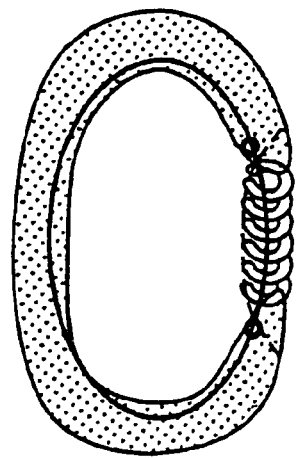
Figure 22A:
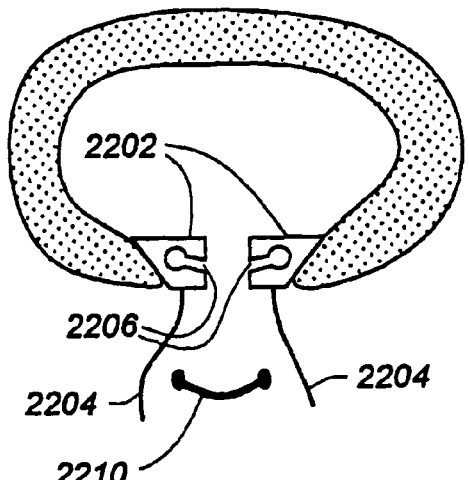
FIG. 22A illustrates the insertion of members adapted to receive a dam component.
Figure 22B:
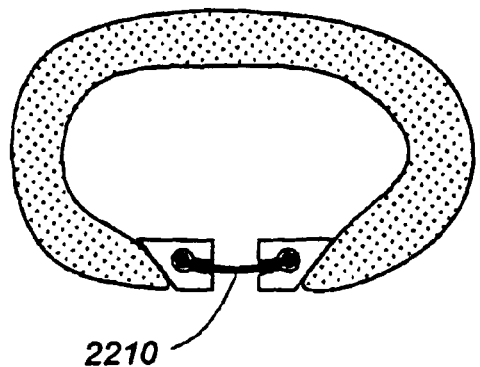
FIG. 22B illustrates the dam of FIG. 22A locked into position.

FIGS. 21A-21C illustrate a different alternative, wherein wires 2102 each having a stop 2104 are first inserted through the annular window, after which blocking beads having snap-in side configurations are journaled onto the wire across the annular hole, as shown in FIG. 21B. FIG. 21C illustrates how, having locked multiple beads onto the wire, the defect is affectively occluded. FIGS. 22A and 22B illustrate the use of a removable dam component. As shown in FIG. 22A, bodies 2202, each having removable handles 2204, are first inserted on the side portions of the defect, each member 2202 including slots, grooves or apertures 2206, configured to receive a dam 2210, which may be made of a rigid or pliable material, depending upon vertebral position, the size of the defect, and other factors. FIG. 22B illustrates the dam 2210 locked in position.

Figure 23D:
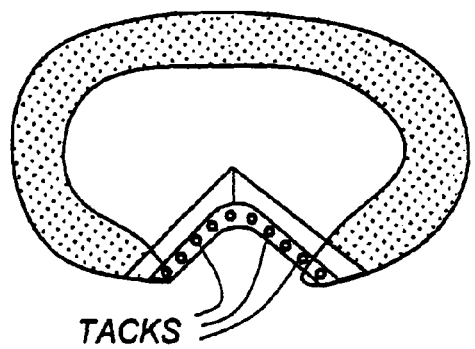
FIG. 23D illustrates the way in which the device of FIGS. 23A-23C, and other embodiments, may be tacked into place with respect to upper and lower vertebrae.
Figure 25:
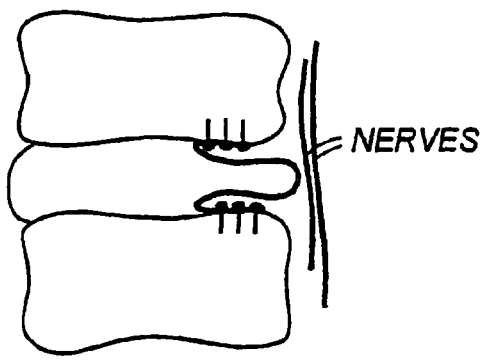
FIG. 25 illustrates a different configuration for the insertion of a resilient dam according to the invention.
Figure 26:
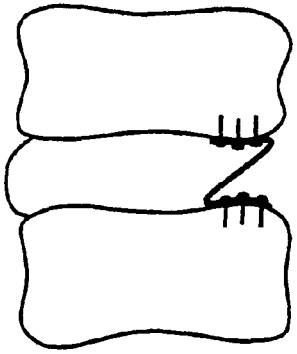
FIG. 26 illustrates an alternative Z-shaped dam of resilient material.
Figure 24B:
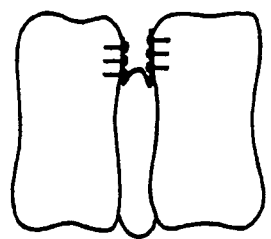
FIG. 24B shows the resilient dam in compression.
Figure 24C:
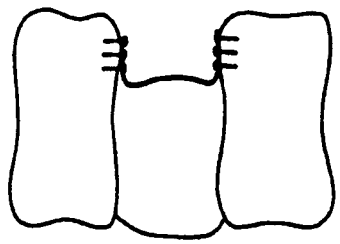
FIG. 24C shows the resilient dam in distraction.
Figure 24A:
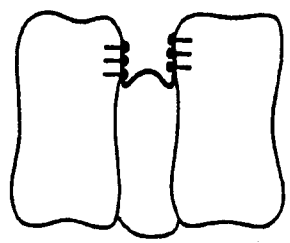
FIG. 24A is a drawing which shows an alternative device that adjusts for compression and distraction, in the form of a resilient dam.
Figure 23B:
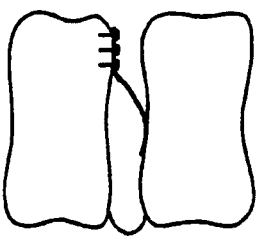
FIG. 23B shows the device of FIG. 23A in compression.
Figure 23C:
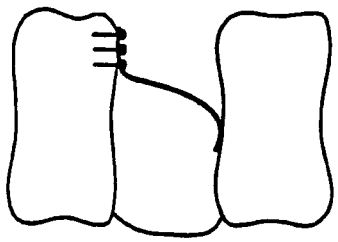
FIG. 23C shows the device of FIG. 23A in distraction.
Figure 23A:
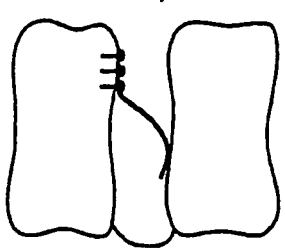
FIG. 23A illustrates one form of defect block that accommodates compression and distraction.

Certain of the following embodiments illustrate how the invention permits the use of a flexible device which allows movement between the vertebrae yet blocks extrusion of nucleus through an annular hole or defect. In FIG. 23A, for example, a flexible element 2302 is tacked into position on the upper vertebrae, as perhaps best seen in FIG. 23D, though it should be apparent that a fixation to the lower vertebrae may also be used. FIG. 23B illustrates how, once the member 2302 is fastened in place, it may flex under compression, but return to a more elongated shape in distraction, as shown in FIG. 23C. The blocking element 2302 may be made from various materials, including shape-memory materials, so long as it performs the function as described herein. FIG. 24A illustrates a different configuration, which is tacked to both the upper and lower vertebrae, and FIGS. 24B and 24C show how the device performs in compression and distraction, respectively. Since devices attached to both the upper and lower vertebrae need not automatically assume a memorized shape, alternative materials may preferably be used, including biocompatible rubbers and other pliable membranes. It is important that the flexible member not be too redundant or stretched so as to compress the nerve, as shown in FIG. 25. FIG. 26 illustrates an alternative Z-shaped installation configuration.

Figure 27A:
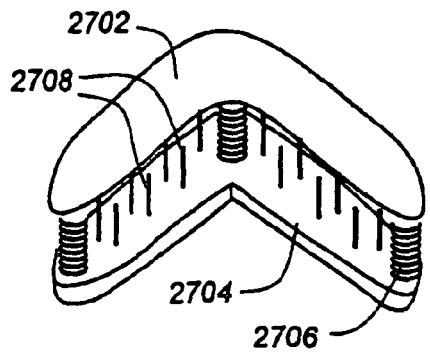
FIG. 27A illustrates the use of interlocking fingers that permit compression and distraction while occluding a defect.
Figure 27B:
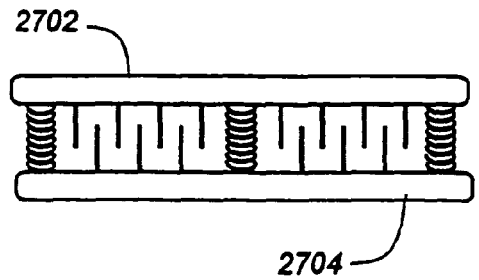
FIG. 27B is a side-view drawing in cross-section of the configuration of FIG. 27.

As an alternative to inherently flexible materials which occlude a defect while accommodating compression and distraction, interleaving members may alternatively be used, as shown in FIGS. 27-28. FIG. 27A is a view from an oblique perspective, showing how upper and lower plate 2702 and 2704 of any suitable shape, may be held together with springs 2706, or other resilient material, between which there is supported interleaving tines 2708. As better seen in FIG. 27B, the springs 2706 allow the upper and lower plates 2702 and 2704 to move toward and away from one another, but at all times, tines 2708 remain interleaving, thereby serving to block a defect.

Figure 28A:
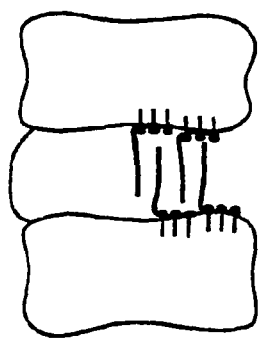
FIG. 28A illustrates an alternative interlocking finger configuration, and the way in which such members are preferably installed.
Figure 28B:
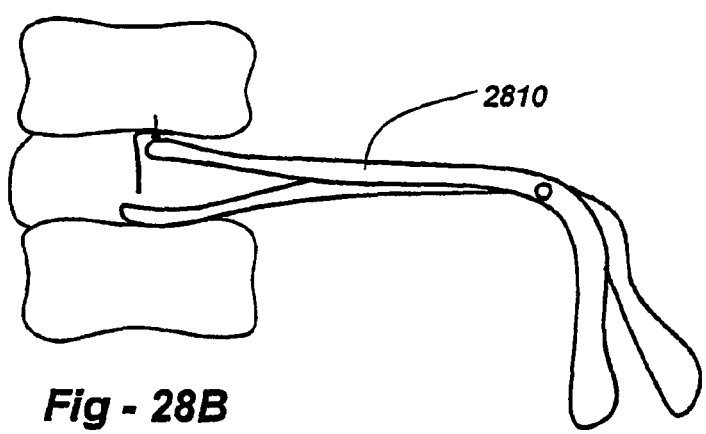
FIG. 28B shows how the first of the multiple members of FIG. 28A is installed.

FIGS. 28A and 28B illustrate the way in which interleaving members or tines are preferably inserted directly to vertebrae. Since each member overlaps with the next, such tines are preferably installed from front to back (or back to front, as the case may be), utilizing a tool such as 2810, as shown in FIG. 28B. The instrument 2810 forces each tack into one vertebrae at a time by distracting against the other vertebrae, thereby applying pressure as the jaws are forced apart, driving the tack into the appropriate vertebrae. The tack may be held into place on the instrument by a friction fit, and may include a barbed end so as not to pull out following insertion.

Figures 29A, 29B:
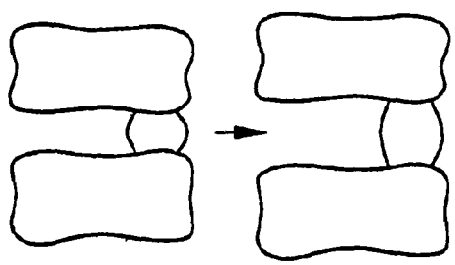
FIG. 29A is a side-view drawing of a non-contained silicon blocking member prior to distraction.
FIG. 29B illustrates the way in which the device of FIG. 29A deforms upon distraction.
Figures 30A, 30B:
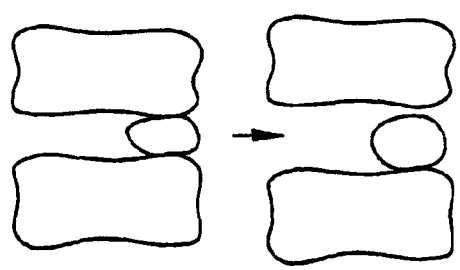
FIG. 30A is a side-view drawing in cross-section illustrating a contained silicon structure prior to distraction.
FIG. 30B illustrates how the contained silicon structure of FIG. 30A remains essentially the same in shape upon distraction.

As a further alternative configuration, a collapsed bag may be placed into the disc space, then filled with a gas, liquid or gel once in position. The bag may be empty, or may contain a stent or expanding shape to assist with formation. In the case of a gel, silicon may be introduced so as to polymerized or solidify. As shown in FIGS. 29A and 29B, the use of a non-contained silicon vessel may be used, but, under distraction, may remain in contact with the vertebrae, thereby increasing the likelihood of a reaction to silicone. The invention therefore preferably utilizes a contain structure in the case of a silicon filler, as shown in FIG. 30A, such that, upon distraction, the vessel remains essentially the same shape, thereby minimizing vertebral contact.

It is noted that, depending upon the configuration, that the invention may make use of a bioabsorbable materials, that is, materials which dissolve in the body after a predetermined period of time. For example, if darts such as those shown in FIGS. 16 and 17 are used, they may bioabsorb following sufficient time for the in-growth of recipient tissue sufficient to occlude the defect independently. Any of the other configurations described herein which might not require certain components in time may also take advantage of bioabsorbable materials. Furthermore, although the invention has been described in relation to preventing the release of natural disc materials, the invention may also be used to retain bone graft for fusion; therapeutic materials including cultured disc cells, glycosaminoglycans, and so forth; and artificial disc replacement materials.

Disc fusions are generally performed for degenerative disc disease, spondylolysis (a stress fracture through the vertebra), spondylolisthesis (slippage of one vertebra on another), arthritis of the facet joints, spinal fractures, spinal tumors, recurrent disc herniations, and spinal instability. The procedure attempts to eliminate motion between vertebra to decrease a patient's pain and/or prevent future problems at the intervertebral level.

Devices such as spinal cages are generally used in conjunction with such procedures to maintain the separation between the vertebrae until fusion occurs. Some surgeons believe that cages are not necessary to maintain the separation, and instead use pedicle screws or hooks and rods to perform this function. Whether or not a cage is used, bone graft is generally introduced through a hole formed in the disc space to achieve an interbody fusion.

Unfortunately, bone material placed into the disc space can extrude through the hole used for insertion. Bone graft extruded through a hole in the posterior portion of the disc may cause nerve root impingement. The procedure to fuse vertebra across the disc space from a posterior approach is known as a PLIF (posterior lumbar interbody fusion). Bone can also be placed into the disc space from an anterior approach ALIF (anterior lumbar interbody fusion). Extruded bone from an anterior approach would not lead to nerve impingement but could decrease the likelihood of a successful fusion by decreasing the volume of bone graft.

The present invention may be used to prevent the loss of the bone graft material associated with fusion techniques, whether or not a cage is used. In this particular regard, however, some of the devices disclosed herein may be more suitable than others. Generally speaking, since the goal is not to preserve disc function and motion, the stent, plug, and patch embodiments may be more appropriate. Although the plug embodiment would be a good choice when there is ample room in the spinal canal to allow insertion, the expandable stent design would be beneficial when plug insertion risks nerve injury. Conversely, since the goal is to maximize the amount of bone inserted into the disc space, the embodiments using hydrogels and elastomers might not be optimum, since such materials may occupy too much space in some circumstances.

Figure 31A:
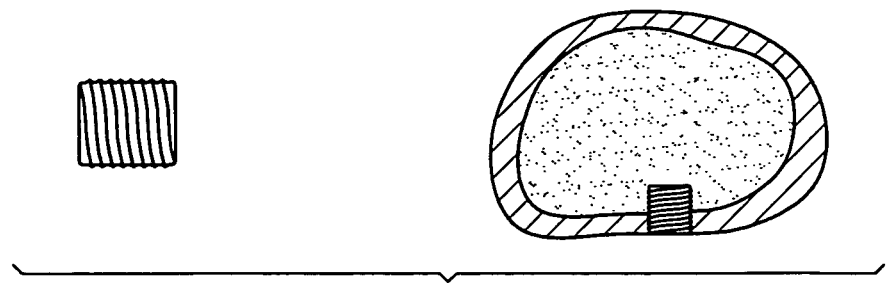
FIG. 31A illustrates the use of threaded metal plug with particular applicability to bone graft retention.
Figure 31B:
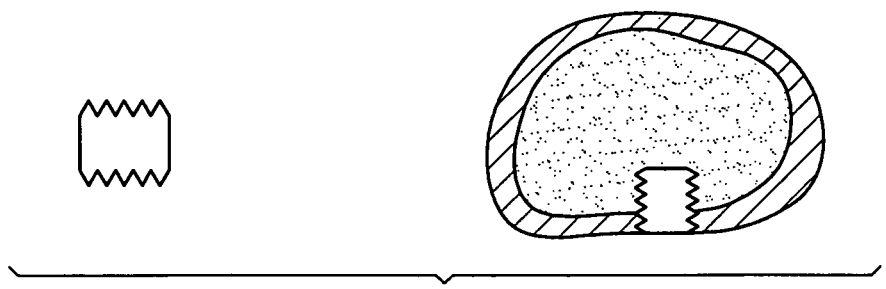
FIG. 31B illustrates a rigid plug with ridges enabling it to be impacted into place.
Figure 31C:
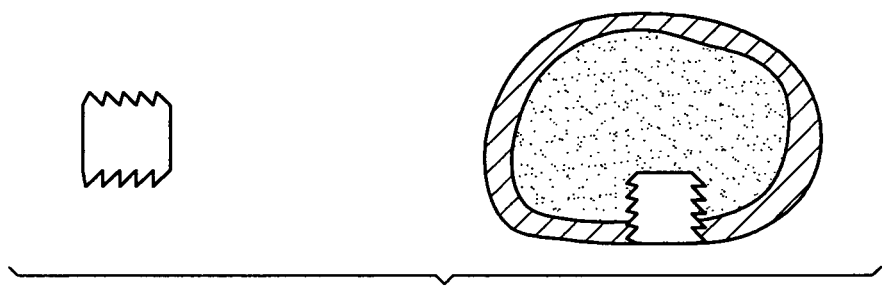
FIG. 31C shows the use of asymmetric ridges to resist posterior migration.
Figure 31D:
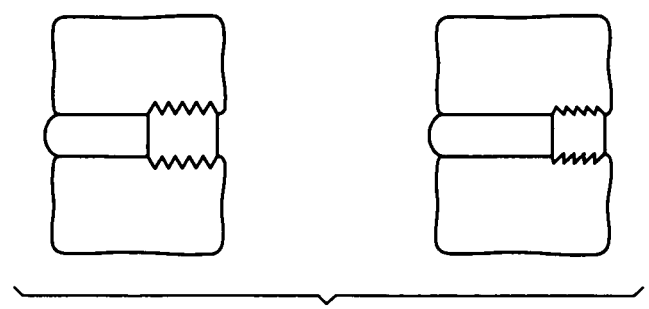
FIG. 31D shows how teeth, screw threads or ridges on certain plug embodiments would extent at least partially into the adjacent vertebra for secure purchase.
Figure 32:
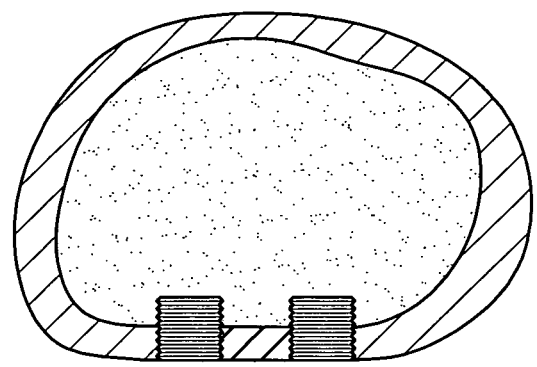
FIG. 32 illustrates bilateral plug positioning according to the invention.

The preferred choice of materials may also be changed since motion is not being maintained. Materials and designs with shape memory may be beneficial. As another example, the polymer plug embodiment may changed to a metal such as titanium. A metal plug may be fabricated with threads and screwed into place, as shown in FIG. 31A, or the device may feature ridges and be impacted into place (FIG. 31B). As shown in FIG. 31C, the ridges may also be asymmetric to resist posterior migration. In all cases, the teeth, screw threads or ridges would extent at least partially into the adjacent vertebra for secure purchase, as depicted in FIG. 31D. Such plugs may also be positioned bilaterally, that is, with two per level, as shown in FIG. 32.

The invention claimed is:

1. A method for treating a defect in an annulus fibrosis of an intervertebral disc, the intervertebral disc being located intermediate an upper vertebra and a lower vertebra, the method comprising the steps of:
   providing a flexible device having a distal end, a proximal end, and a midsection extending between the distal end and the proximal end, the midsection having a first surface and a second surface;
   inserting the flexible device into the defect in the annulus fibrosis so that the distal end is positioned within an intradiscal space, the midsection extends across and beyond the periphery of the area defining the defect in the annulus fibrosis and the first surface of the midsection faces the nucleus; and
   attaching the proximal end of the flexible device to one of the upper vertebra or lower vertebra;
   wherein the distal end of the flexible device resiliently engages and rests against an endplate of the other of the upper vertebra or lower vertebra,
   wherein said flexible device prevents escape of nucleus pulposus through the defect in the annulus fibrosis; and
   wherein the distal end of said flexible device maintains contact with the vertebral endplate of the other of the upper vertebra or lower vertebra under distraction of the intervertebral disc.

2. The method of claim 1, wherein the flexible device is made from a shape memory material.

3. The method of claim 1, wherein the proximal end of said flexible device is attached to the upper vertebra.

4. The method of claim 3, wherein the distal end of said flexible device engages and rests against the endplate of the lower vertebra.

5. The method of claim 4, wherein the distal end of said flexible device slidingly engages the endplate of the lower vertebra.

6. The method of claim 3, wherein the proximal end of said flexible device is attached to the endplate of the upper vertebra.

7. The method of claim 6, wherein the proximal end of said flexible device is attached to the endplate of the upper vertebra by at least one fastener which extends transverse to the endplate of the upper vertebra.

8. The method of claim 1, wherein said proximal end of said flexible device is attached to the lower vertebra.

9. The method of claim 8, wherein the proximal end of said flexible device is attached to the endplate of the lower vertebra.

10. The method of claim 9, wherein the proximal end of said flexible device is attached to the endplate of the lower vertebra by at least one fastener which extends transverse to the endplate of the lower vertebra.

11. The method of claim 8, wherein the distal end of said flexible device engages the endplate of the upper vertebra.

12. The method of claim 11, wherein the distal end of said flexible device slidingly engages the endplate of the upper vertebra.

13. The method of claim 1, wherein said flexible device allows movement between the upper vertebra and lower vertebra.

14. The method of claim 1, wherein said flexible device flexes under compression of the intervertebral disc.

15. The method of claim 1, wherein said flexible device returns to an elongated shape under distraction of the intervertebral disc.

16. The method of claim 1, wherein the distal end of said flexible device maintains contact with the vertebral endplate of the other of the upper vertebra or lower vertebra under compression of the intervertebral disc.

17. The method of claim 1, wherein the distal end of said flexible device moves relative to a vertebral endplate of the other of the upper vertebra or lower vertebra under compression of the intervertebral disc.

18. The method of claim 1, wherein the distal end of said flexible device moves relative to a vertebral endplate of the other of the upper vertebra or lower vertebra under distraction of the intervertebral disc.

* * * * *